(12) United States Patent
Wang et al.

(10) Patent No.: US 10,234,380 B1
(45) Date of Patent: Mar. 19, 2019

(54) BACKGROUND RADIANCE ESTIMATION AND GAS CONCENTRATION-LENGTH QUANTIFICATION METHOD FOR OPTICAL GAS IMAGING CAMERA

(71) Applicant: Konica Minolta Laboratory U.S.A., Inc., San Mateo, CA (US)

(72) Inventors: Leiming Wang, Foster City, CA (US); Ting Xu, Foster City, CA (US)

(73) Assignee: Konica Minolta Laboratory U.S.A., Inc., San Mateo, CA (US)

( * ) Notice: Subject to any disclaimer, the term of this patent is extended or adjusted under 35 U.S.C. 154(b) by 0 days.

(21) Appl. No.: 15/720,708

(22) Filed: Sep. 29, 2017

(51) Int. Cl.
*G01N 21/3504* (2014.01)
*G01M 3/38* (2006.01)

(52) U.S. Cl.
CPC ......... *G01N 21/3504* (2013.01); *G01M 3/38* (2013.01); *G01N 2021/3509* (2013.01)

(58) Field of Classification Search
CPC ............... G01N 21/3504; G01N 21/39; G01N 2201/025; G01N 2021/0314; G01N 33/0004; G01N 21/01; G01N 1/2273; G01N 1/26; G01N 33/0009; G01N 33/0062; G01N 2021/1795; G01N 21/31; G01N 2021/399; G01N 21/33; G01N 33/0075; G01N 2021/1793; G01N 21/53; G01J 2005/0077; G01J 5/0014; G01J 5/0806; G01J 2003/2826; G01J 3/0208; G01J 3/2823; G01J 3/4531; G01J 9/0215; G01B 21/20; G01B 9/02001; G01B 9/02041; G01B 9/02089
See application file for complete search history.

(56) References Cited

U.S. PATENT DOCUMENTS

2011/0038507 A1\* 2/2011 Hager .................... G01N 21/33
382/100
2014/0008526 A1  1/2014 Zeng et al.
2017/0363541 A1\* 12/2017 Sandsten ........... G01N 21/3504

FOREIGN PATENT DOCUMENTS

WO  2017/104607 A1  6/2017

OTHER PUBLICATIONS

D. Tseng et al; "Plume Extraction Using Entropic Thresholding and Region Growing"; Pattern Recognition, vol. 26, No. 5, pp. 805-817; May 1993 (13 pages).

(Continued)

*Primary Examiner* — Michael P Stafira
(74) *Attorney, Agent, or Firm* — Osha Liang LLP

(57) ABSTRACT

A gas concentration-length quantification method may include acquiring a first image including a gas plume with a camera; identifying and segmenting pixels corresponding to the gas plume in the first image; creating a mask image corresponding to the first image, where only pixels of the mask image corresponding to the gas plume in the first image have non-zero values; generating a background image corresponding to the first image using an image inpainting algorithm with the first image and the mask image as inputs; calculating a gas concentration-length for each pixel corresponding to the gas plume in the first image, based on the first image and the background image data; and triggering an alert when the gas concentration-length for at least one pixel exceeds a threshold level.

19 Claims, 7 Drawing Sheets

(56) References Cited

OTHER PUBLICATIONS

E. Hirsch et al; "Detection of Gaseous Plumes in IR Hyperspectral Images Using Hierarchical Clustering"; Applied Optics, vol. 46, No. 25, pp. 6368-6374; Sep. 1, 2007 (7 pages).
H. Hu et al; "Multi-Class Graph Mumford-Shah Model for Plume Detection Using the MBO Scheme"; Energy Minimization Methods in Computer Vision and Pattern Recognition; 2015 (14 pages).
A. Telea; "An Image Inpainting Technique Based on the Fast Marching Method"; Journal of Graphics Tools, vol. 9, No. 1, pp. 25-36; 2004 (12 pages).
M. Bertalmio et al; "Navier-Stokes, Fluid Dynamics, and Imaging and Video Inpainting"; 2001 IEEE Conference on Computer Vision and Pattern Recognition (CVPR); Kauai, Hawaii, USA; Dec. 8-14, 2001 (8 page).
G. Larsson et al; "Learning Representations for Automatic Colorization"; 2016 European Conference on Computer Vision, pp. 577-593; Sep. 2016 (29 pages).
R. Zhang et al; "Colorful Image Colorization"; 2016 European Conference on Computer Vision, pp. 649-666; Sep. 2016 (29 pages).
S. Iizuka et al; "Let There Be Color!: Joint End-To-End Learning of Global and Local Image Priors for Automatic Image Colorization with Simultaneous Classification"; ACM Transactions on Graphics (TOG), vol. 35, No. 4, art. 110; Jul. 2016 (11 pages).

\* cited by examiner

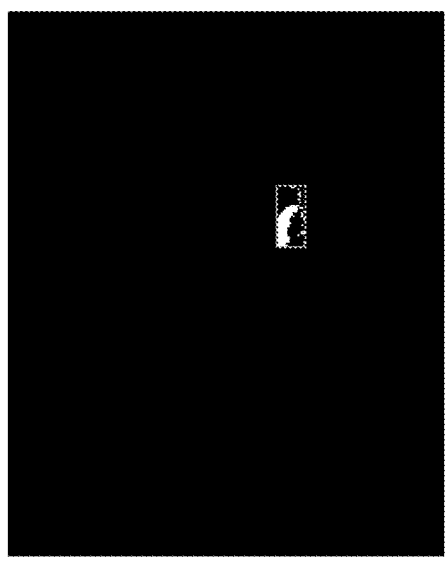
Fig. 4A
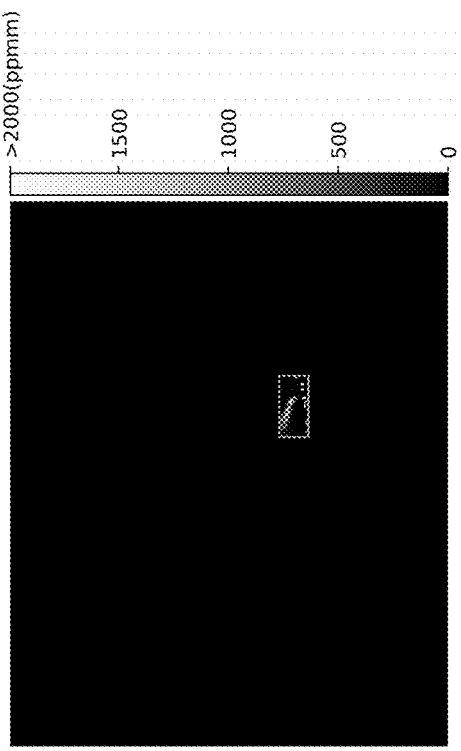
Fig. 4B
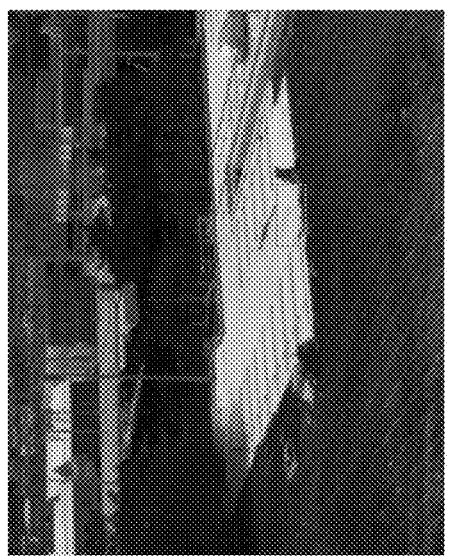
Fig. 4C
Fig. 4D

BACKGROUND RADIANCE ESTIMATION AND GAS CONCENTRATION-LENGTH QUANTIFICATION METHOD FOR OPTICAL GAS IMAGING CAMERA

BACKGROUND

In recent years, infrared (IR) optical gas imaging (OGI) cameras have been tools extensively used for gas leakage detection and monitoring due to better visualization of gas leaks, reduced inspection time, and improved safety as compared to conventional gas sensing techniques, such as catalytic detectors.

In addition to the practical qualitative use of IR OGI cameras, quantitative use has been suggested. For example, it is possible to quantify a gas concentration-length (a concentration integrated along a path length, e.g., in units of parts per million-meter, or ppm·m) of an imaged plume with appropriate calibration. The gas concentration-length may also be referred to as a gas concentration path length (CPL).

IR OGI is one of two methods recognized by the U.S. Environmental Protection Agency (EPA) for gas Leak Detection and Repair (LDAR) surveys in the U.S. oil and gas industry, the second being EPA Method 21.

SUMMARY

This summary is provided to introduce a selection of concepts that are described further in the detailed description below. This summary is not intended to identify key or essential features of the claimed subject matter, nor is it intended to be used as an aid in limiting the scope of the claimed subject matter.

In one or more embodiments of the present invention, a gas concentration-length quantification method may comprise acquiring a first image including a gas plume with a camera; identifying and segmenting pixels corresponding to the gas plume in the first image; a mask image corresponding to the first image, wherein only pixels of the mask image corresponding to the gas plume in the first image have non-zero values; generating a background image corresponding to the first image using an image inpainting algorithm with the first image and the mask image as inputs; calculating a gas concentration-length for each pixel corresponding to the gas plume in the first image, based on the first image and the background image data; and triggering an alert when the gas concentration-length for at least one pixel exceeds a threshold level.

In one or more embodiments of the present invention, a gas concentration-length quantification system may comprise a camera; a processing unit connected to the camera, wherein the processor performs: reading a first image including a gas plume from the camera; identifying and segmenting pixels corresponding to the gas plume in the first image; creating a mask image corresponding to the first image wherein only pixels of the mask image corresponding to the gas plume in the first image have non-zero values; generating a background image corresponding to the first image using an image inpainting algorithm with the first image and the mask image as inputs; calculating a gas concentration-length for each pixel corresponding to the gas plume in the first image, based on the first image and the background image data; and triggering an alert when the gas concentration-length for at least one pixel exceeds a threshold level.

In one or more embodiments of the present invention, a non-transitory computer readable medium (CRM) may store computer readable program code embodied therein that: reads a first image including a gas plume; identifies and segments pixels corresponding to the gas plume in the first image; creates a mask image corresponding to the first image wherein only pixels of the mask image corresponding to the gas plume in the first image have non-zero values; generates a background image corresponding to the first image using an image inpainting algorithm with the first image and the mask image as inputs; calculates a gas concentration-length for each pixel corresponding to the gas plume in the first image, based on the first image and the background image data; and triggers an alert when the gas concentration-length for at least one pixel exceeds a threshold level.

Other aspects and advantages will be apparent from the following description and the appended claims.

BRIEF DESCRIPTION OF DRAWINGS

Embodiments of the invention will be described with reference to the accompanying drawings. However, the accompanying drawings illustrate only certain aspects or implementations of one or more embodiments of the invention by way of example and are not meant to limit the scope of the claims.

FIGS. 4A-4D show an example of a gas concentration-length method in accordance with one or more embodiments of the invention.

DETAILED DESCRIPTION

Figure 1A:
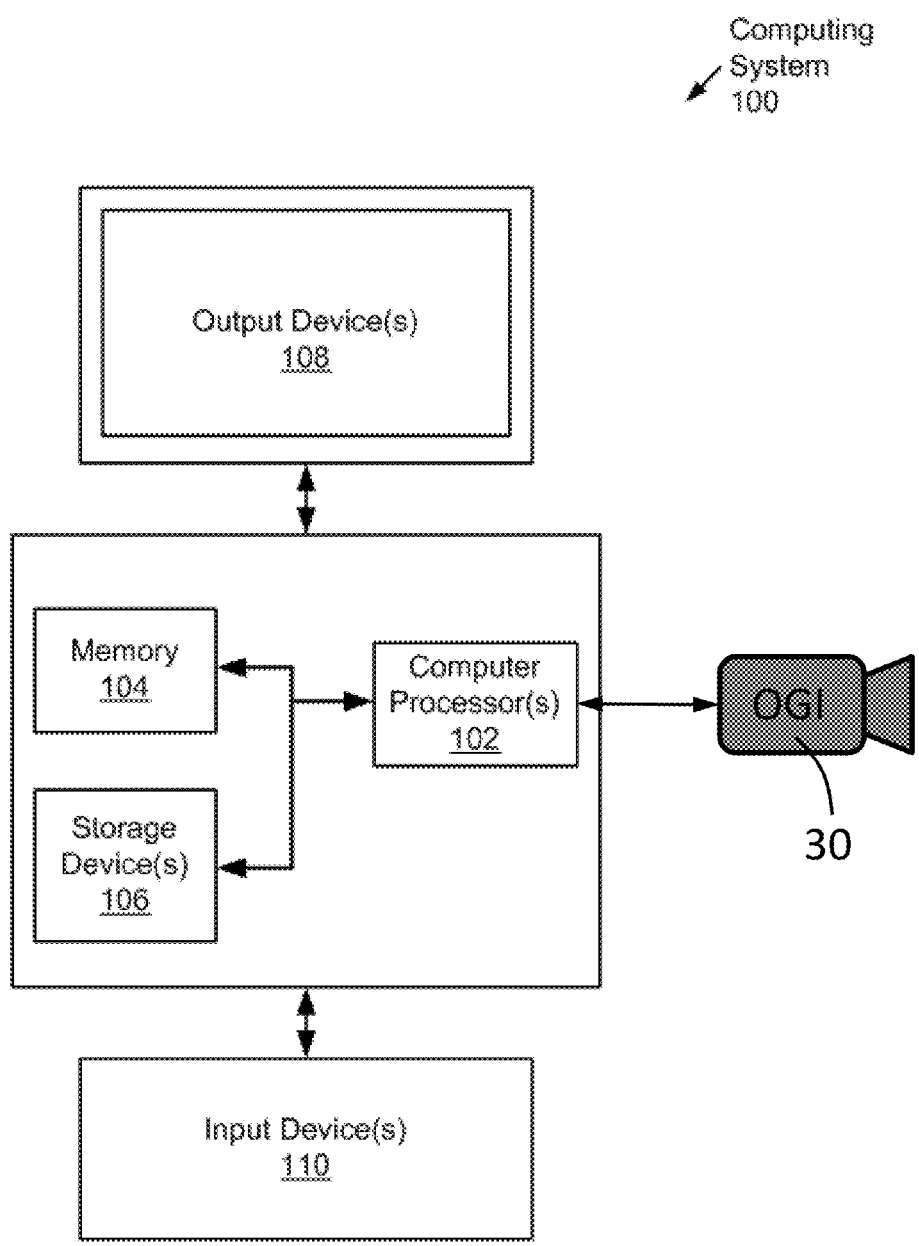
FIGS. 1A-1C show gas concentration-length quantification systems in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Further, any reference to connection may mean either an indirect or direct connection. Thus, if a first component is coupled to a second component, that connection may be through a direct connection, or through an indirect connection via other components, devices, and connections. Electronic devices may be connected via wires or wirelessly. Electronic devices may be connected via a network, for example, a local area network (LAN), a wide area network (WAN), the Internet, or the like. Further, the terms "axial" and "axially" generally mean along or parallel to a central or longitudinal axis, while the terms "radial" and "radially" generally mean perpendicular to a central longitudinal axis.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the invention provide for a method, a system, and a non-transitory computer readable medium for quantifying gas concentration-length using at least one image frame acquired by a camera. In one or more embodiments, the camera is an optical gas imaging camera sensitive to infrared radiation.

FIG. 1A shows a gas concentration-length quantification system in accordance with one or more embodiments of the invention. An optical gas imaging (OGI) camera 30 may be connected to one or more computer processors 102. The connection between the OGI camera 30 and computer processors 102 may be made with wires or wirelessly. The one or more processors may be included in a computing system 100.

Embodiments of the invention may be implemented using virtually any type of computing system 100, regardless of the platform being used. For example, the user computing devices may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 1A, the computing system 100 may include one or more processor(s) 102, associated memory 104 (e.g., random access memory (RAM), cache memory, flash memory, etc.), one or more storage device(s) 106 (e.g., a hard disk, an optical drive such as a compact disk (CD) drive or digital versatile disk (DVD) drive, a flash memory stick, etc.), and numerous other elements and functionalities. The processor(s) 102 may be an integrated circuit for processing instructions. For example, the processor(s) 102 may be one or more cores, or micro-cores of a processor.

The computing system 100 may also include one or more input device(s) 110, such as a touchscreen, keyboard, mouse, microphone, touchpad, electronic pen, or any other type of input device. Further, the computing system 100 may include one or more output device(s) 108, such as a screen (e.g., a liquid crystal display (LCD), a plasma display, touchscreen, cathode ray tube (CRT) monitor, projector, or other display device), a printer, external storage, or any other output device. One or more of the output device(s) 108 may be the same or different from the input device(s). The output device(s) 108 may include a light, for example a flashing red light, a horn, a buzzer, or the like that may be used as an alert when a gas concentration-length exceeds a threshold level. The output device(s) may generate and/or receive a facsimile (fax), an email, a Short Message Service (SMS) text, or the like.

Figure 1B:
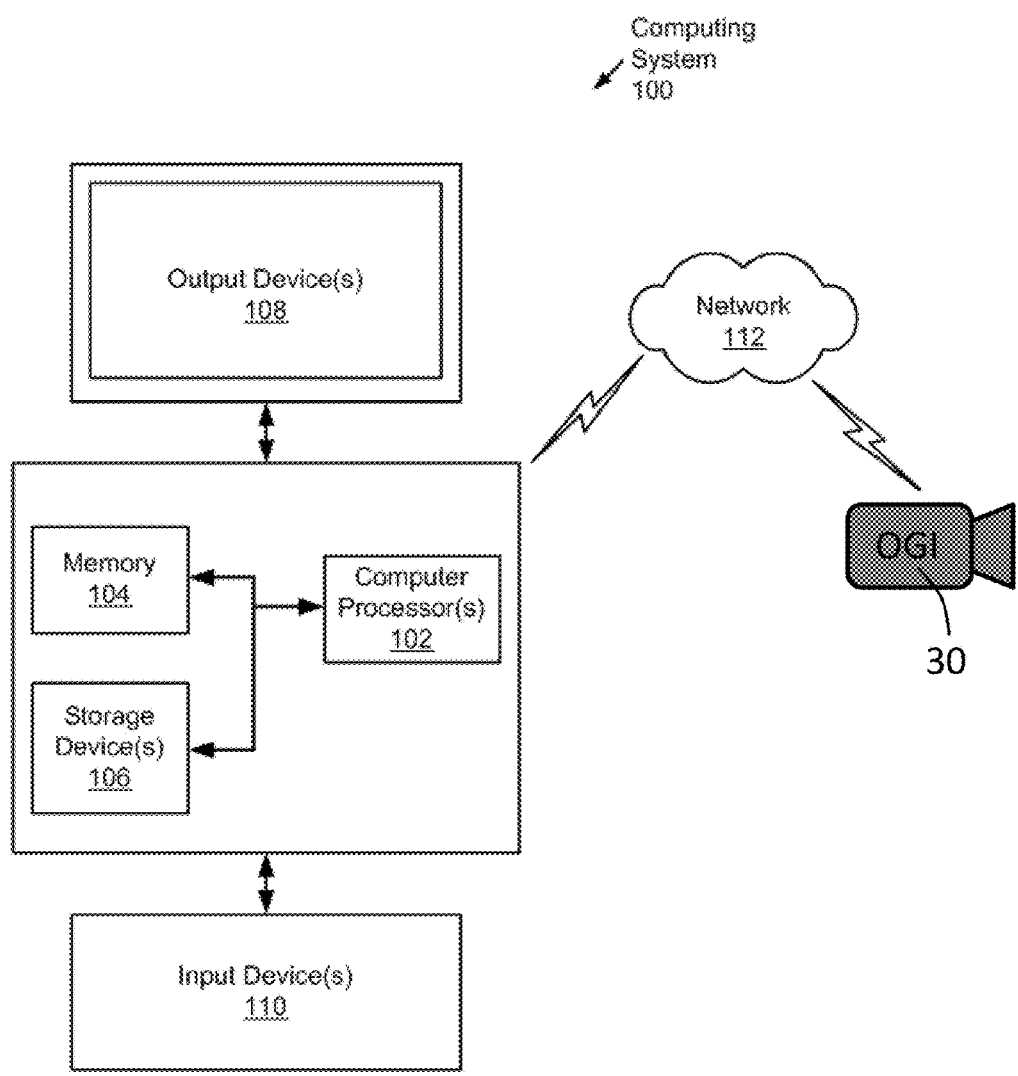

FIG. 1B shows that, in accordance with one or more embodiments, the computing system 100 may be connected to a network 112 (e.g., a local area network (LAN), a wide area network (WAN) such as the Internet, mobile network, or any other type of network) via a network interface connection (not shown). The input and output device(s) may be locally or remotely (e.g., via the network 112 connected to the processor(s) 102, memory 104, and storage device(s) 106. The OGI camera 30 may be connected to one or more computer processors 102 by the network 112. Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s) 102, performs one or more embodiments of the invention. Also, all discussed steps performed by a processor executing software instructions may, in one or more embodiments, be in the form of hardware such as circuitry. Those skilled in the art will appreciate that the hardware may be comprised of application-specific integrated circuits or other appropriate circuitry.

Further, one or more elements of the aforementioned computing system 100 may be located at a remote location and connected to the other elements over a network 112. Further, one or more embodiments of the invention may be implemented on a distributed system having a plurality of nodes, where each portion of the invention may be located on a different node within the distributed system. In one or more embodiments of the invention, the node corresponds to a distinct computing device. Alternatively, the node may correspond to a processor with associated physical memory. The node may alternatively correspond to a processor or micro-core of a processor with shared memory and/or resources.

Figure 1C:
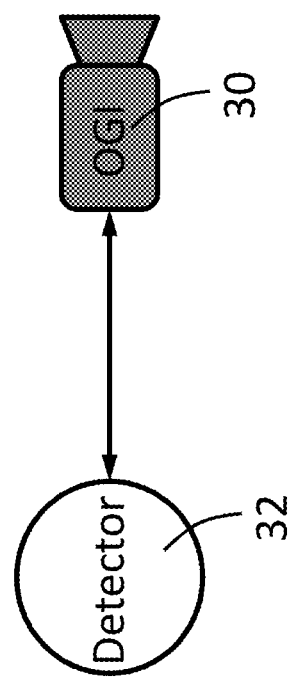

FIG. 1C shows an OGI camera 30 connected to a detector 32. The detector may be of the type commonly used in residential or industrial settings, such as a smoke detector, a heat detector, a carbon monoxide detector, or the like. The connection may be wired or wireless and may include a connection via a network. In one or more embodiments, the OGI camera 30 may be integrated into the detector 32. In one or more embodiments, the OGI camera 30 may be integrated on an integrated circuit.

In one or more embodiments, the OGI camera 30 may be used to capture images for gas concentration-length quantification from commercial, industrial, marine, residential, or rural environments, among others.

Figure 2:
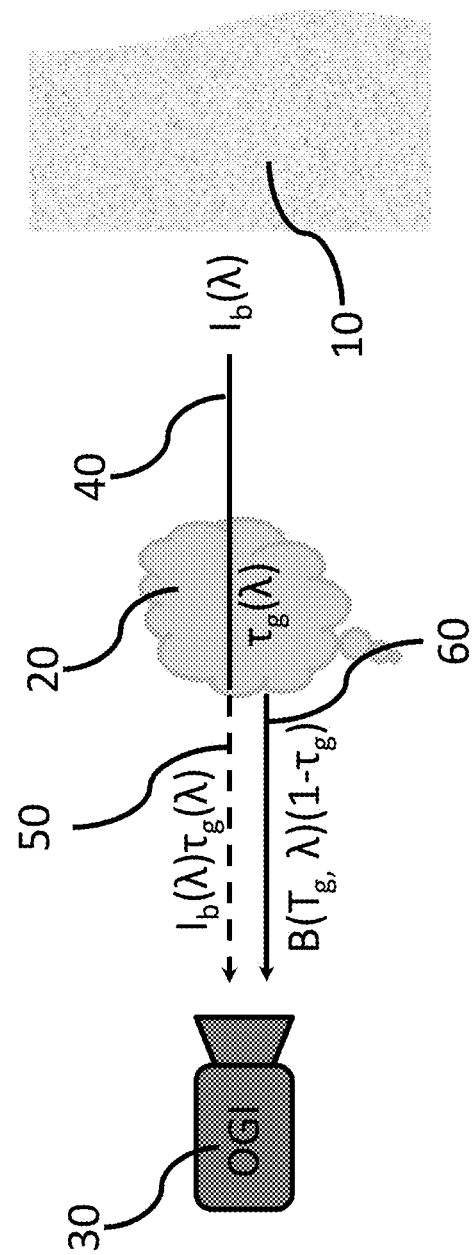
FIG. 2 is a schematic diagram showing the radiative transfer model mechanism of gas detection and quantification in accordance with one or more embodiments of the invention.

FIG. 2 shows a schematic diagram of gas leak imaging by OGI and the physical basis (known as the radiative transfer model) for gas concentration-length (thickness or length integrated concentration, e.g., in units of parts per million-meter, or ppm·m) quantification. An OGI camera may be equipped with a band-pass filter that corresponds to the absorption band of the target gas. The target gas may be, for example, methane, sulfur hexafluoride, carbon monoxide, carbon dioxide, among others. One or more of these target gases may be detected, for example, in an oil and gas industry setting. However, one or more embodiments of the present invention may be applied to other settings, for example, including residential settings.

Radiance 40 from the background 10, $I_b(\lambda)$, where $\lambda$ denotes the wavelength of the radiation, passes through a gas plume 20, where the intensity of the radiance from the background 40 may be attenuated by gas absorption. The absorption by gas plume 20 may be characterized by a transmittance coefficient $\tau_g(\lambda)$ so that the transmitted radiance 50 reaching the OGI camera 30 becomes $I_b(\lambda)\tau_g(\lambda)$. The transmittance coefficient $\tau_g(\lambda)$ is related to the gas concentration-length $\gamma$ through the Beer-Lambert law: $\tau_g(\lambda)=\exp(-\gamma\alpha(\lambda))$, wherein the absorbance spectrum $\alpha(\lambda)$ is unique and known for each gas species.

Meanwhile, the infrared-absorbing gas plume 20 also radiates thermal energy 60, which is characterized by the product of the blackbody radiation (Planck function) $B(\tau_g, \lambda)$) at the temperature of the gas ($T_g$) and the emissivity of the gas ($1-\tau_g$). Thus, in one or more embodiments, the OGI camera 30 may record the background radiance $I_b(\lambda)$ modulated by the gas plume 20 absorption:

$$I_{recorded}(\lambda)=I_b(\lambda)\tau_g(\lambda)+B(\tau_g,\lambda)(1-\tau_g(\lambda)) \qquad (1)$$

Depending on the relative temperature difference between the gas plume 20 and the background 10, the gas plume 20 may be visualized as dark or bright contrast against the background 10 in the recorded image.

The simplified radiative transfer equation (1) also may provide the physical basis for quantification of the transmittance coefficient $\tau_g(\lambda)$, and subsequently quantification of the concentration-length of the gas plume 20, provided that $I_b(\lambda)$ and $B(T_g, \lambda)$ are known in Eqn. (1). $B(T_g, \lambda)$ may be readily obtained by measuring the temperature of the gas plume 20 and calculating with the Planck function. Thus, obtaining the background radiance $I_b(\lambda)$ is the key challenge for gas concentration-length quantification in optical gas imaging (OGI). The following are three possible approaches of background radiance estimation employed in one or more embodiments of the present invention.

One approach to background radiance estimation may be to acquire a separate imaging measurement of the background while the gas is not present in the scene (See, e.g., U.S. Patent Publ. No. 2014/0008526). However, this method is limited to a controlled laboratory environment and may not be applicable for field application where the background radiance varies with time and the gas leak is not controllable.

A second approach to background radiance estimation may be by a second IR image acquired with spectral filtering that does not produce a response from the target gas (See, e.g., U.S. Patent Publ. No. 2014/0008526). However, this method requires a second OGI camera with a different band-pass filter, or a multi-spectral or hyper-spectral OGI camera at high cost.

A third approach to background radiance estimation may be by temporal analysis of chronologically arranged pixel data, in which background radiance 40 is approximated by temporal variation amplitude caused by the gas disturbance for predetermined pixels in a sequence of video images (See, e.g., WO2017104607 A1). However, this method requires a series of video images. As a result, this method may be susceptible to environmental conditions and need to process many images. Also, the process may be difficult to automate and extend to every pixel of the gas plume 20.

In one or more embodiments of the present invention, a method for background radiance estimation in an optical gas image may use a computer vision technique of "image inpainting," and the gas concentration-length quantification process based on that. With this method, a background image may be generated automatically. The method requires as input only a single IR image in which a gas plume can be visualized and segmented.

Thus, the method may have the advantage of eliminating the need of expensive multi- or hyper-spectral OGI cameras and/or computationally time-consuming chronological data analysis. Another advantage of one or more embodiments is that the method may be solely based on image processing and, thus, is not sensitive to environmental conditions. Further, the method is not required to process time series images for gas concentration-length quantification. Another advantage of one or more embodiments of this method is that the method may provide a background radiance estimation method for gas concentration-length quantification in a single-band OGI gas leak imaging application.

Figure 3:
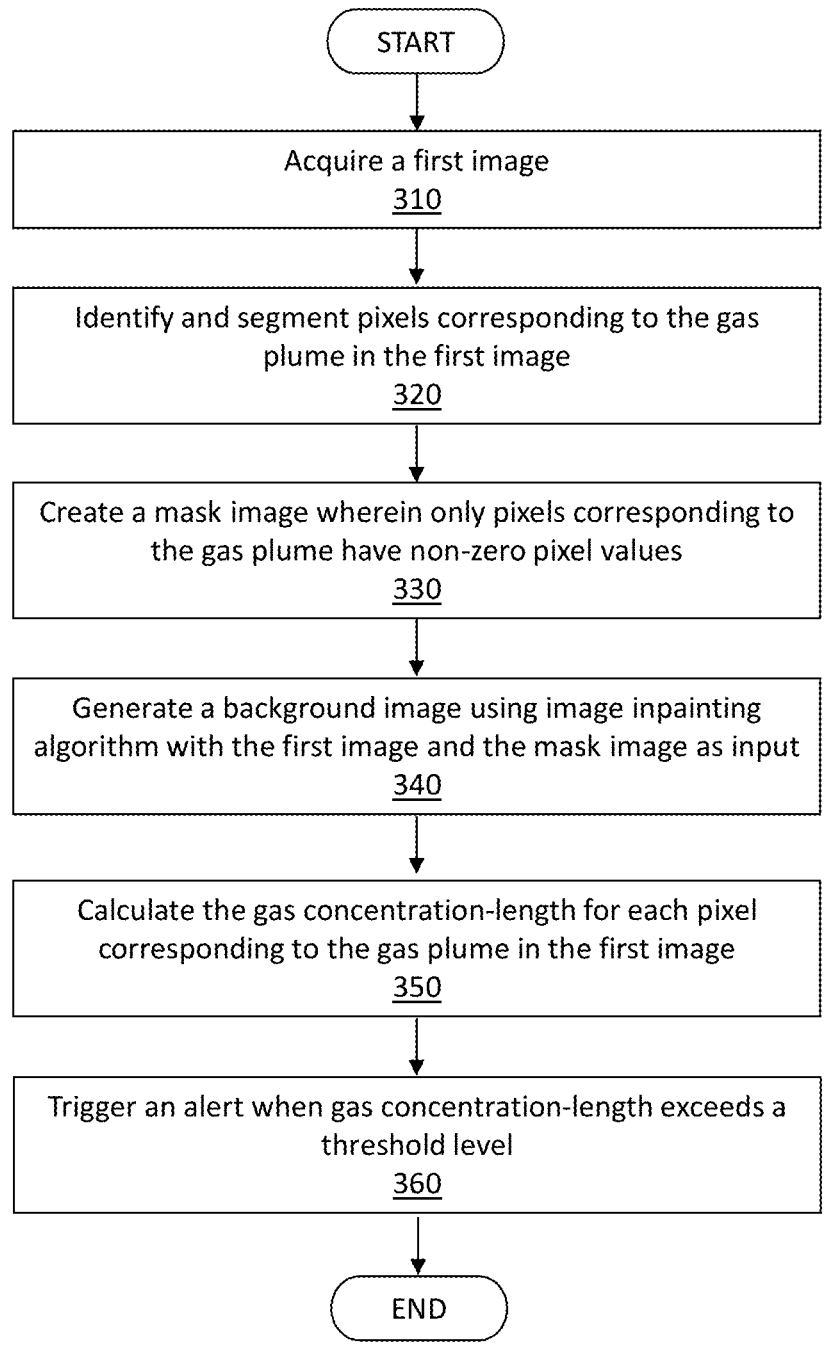
FIG. 3 is a flowchart of a gas concentration-length quantification method in accordance with one or more embodiments of the invention.

FIG. 3 is a flowchart describing a method of gas concentration-length quantification based on a background radiance estimation using an image inpainting method according to one or more embodiments. Image inpainting may also be known as image interpolation or video interpolation.

In step 310, an image containing a gas plume may be acquired. In one or more embodiments, the image may be an infrared image acquired by an OGI camera. For clarity of discussion and to distinguish the image from other images, the image will be referred to hereinafter as an infrared (IR) image. However, the term is not intended to restrict to the image being infrared. It is readily apparent that images of other radiation wavelengths may be included. A single IR image may be acquired, or a sequence of IR images may be acquired as with a sequence of video image frames. The pixel intensities in the IR image may be calibrated to represent either the temperature or the radiance value of the scene using known calibration data of the OGI camera.

In one or more embodiments, a region of interest (ROI) enclosing the gas plume, or gas leak source, may be manually selected for subsequent process. By doing analysis only within the ROI, computational speed may be improved.

In one or more embodiments, the ROI may be selected to enclose an area where the background scene is substantially homogeneous (e.g., the rectangular box in FIG. 4A). By selecting an ROI where the background scene is substantially homogeneous, the accuracy of the background radiance calculation may be improved.

In step 320, the method identifies and segments pixels corresponding to the gas plume in the IR image. Hereinafter, these pixels may be referred to as "gas pixels."

Identification of gas pixels may be done using common image segmentation methods, such as thresholding and region growing, divisive hierarchical clustering, and energy minimization in Mumford-Shah variational formulation, or the like.

Alternatively, in one or more embodiments, gas pixels may be identified by a chronological analysis of a sequence of video frames, for example, as described in WO2017104607 A1. This method of identification may be more effective in IR images in which the contrast of the gas plume against the background is weak.

In step 330, a mask image corresponding to the IR image may be created based on the gas pixels segmentation in step 220 in which only pixels corresponding to the gas plume have non-zero values. In one or more embodiments, the mask image is a binary image. An example of a mask image created based on gas pixels of FIG. 4A is shown in FIG. 4B. The rectangular box indicates the same defined ROI shown in FIG. 4A.

In step 340, the method may calculate a new image representing the background data (temperature or radiance), using image inpainting algorithms with the IR image and the created mask image as input. The background data may also be referred to as the background image. FIG. 4C shows an example of a background image. This background image is generated using an image inpainting algorithm with the IR image of FIG. 4A and the mask image of FIG. 4B as inputs. The rectangular box indicates the same defined ROI shown in FIGS. 4A and 4B. In one or more embodiments, the image inpainting algorithm may be the Telea algorithm. The Telea algorithm may be found in "An image inpainting technique based on the fast marching method" by Alexandru Telea and published in Volume 9 of the Journal of Graphics Tools, pages 25-36, in 2004. In one or more embodiments, the image inpainting algorithm may be the Navier-Stokes algorithm. The Navier-Stokes algorithm may be found in "Navier-Stokes, fluid dynamics, and imaging and video inpainting" by Marcelo Bertalmio et al. and published in the Proceedings of IEEE CVPR (Computer Vision and Pattern Recognition) in 2001.

In step 350, the method may calculate a gas concentration-length at each pixel using the data of the IR image, the generated background image, and the temperature of the gas plume. In one or more embodiments, the gas temperature may be measured with a thermometer or may be assumed to be at the same as the temperature of the ambient air.

The calculation of a gas concentration-length may be based on the radiative transfer model as described above, and may use the procedure disclosed in WO2017104607 A1. An example result is shown in FIG. 4D in which the calculated gas concentration-length value at each gas pixel is expressed in a gray-scale color. The calculated image of FIG. 4D is based on the IR image in FIG. 4A and the calculated background image data in FIG. 4C. The rectangular box indicates the same defined ROI shown in FIGS. 4A-4C.

In one or more embodiments, the method described with reference to the flowchart in FIG. 3 may repeat steps 210 through 250 a plurality of times in order to process a plurality of images such as may be generated by a video stream.

In step 360, the method may trigger an alert when the gas concentration-length of at least one pixel exceeds a threshold level. An alert may take many forms and may include a plurality of forms. One of the forms of alert may be a colored light, e.g., a red light, on a user console. The light may illuminate and/or flash. An alert may be audible, e.g., a bell, a siren, a horn, or the like. An alert may be an email, a facsimile (fax), a Short Message System (SMS) text message, a telephone communication, or the like. An alert may display on a computer display, a mobile device, a mobile phone, or the like. An alert may be provided to one or more locations and/or one or more users. An alert may be transmitted through a wired and/or a wireless system or network. The alert may be directed to a user and/or to another device that may automatically perform one or more functions is response to the alert.

Figure 5:
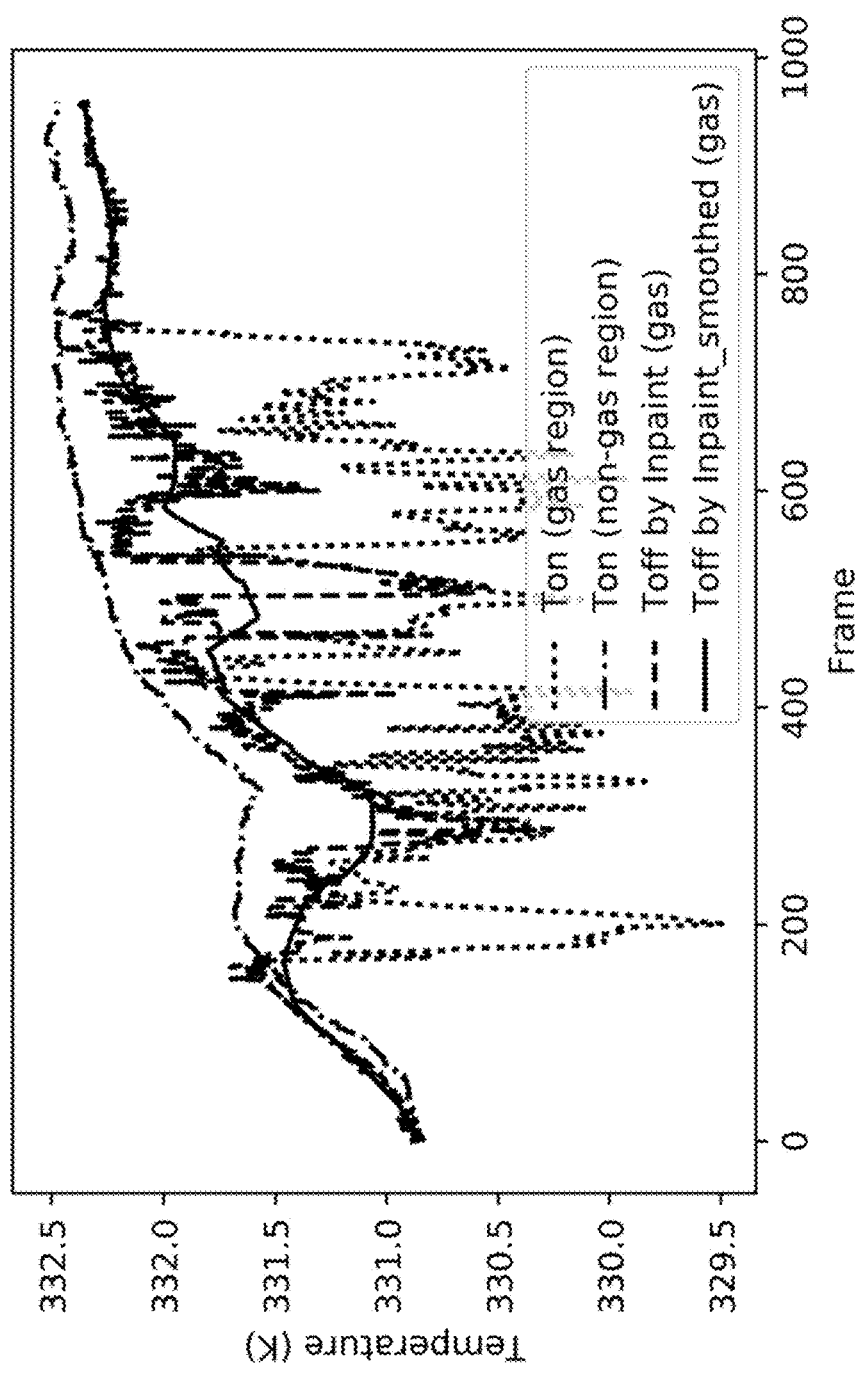
FIG. 5 shows an example calculation in accordance with one or more embodiments of the invention.

FIG. 5 shows the estimated background temperature using the image inpainting method for a predetermined gas pixel in a sequence of 960 video image frames, demonstrating that the method reproduces the overall temporal variation of the background temperature. Background radiance may be calculated from the background temperature using the Planck equation. The curve labelled "Ton (gas region)" and depicted using short dashes displays the OGI-recorded temperature variation at the predetermined gas pixel as a function of video image frame number when gas is present. The long-dashed curve labelled "Toff by Inpaint (gas)" is the estimated background temperature of the predetermined gas pixel using the image inpainting method. The solid line labelled "Toff by Inpaint_smoothed (gas)" is a smoothed version of "Toff by Inpaint (gas)." For comparison, the OGI-recorded temperature variation at a non-gas pixel, i.e., a pixel without gas presence, is represented by the dot-dash curve labelled "Ton (non-gas region)."

In one or more embodiments, the accuracy of the background radiance estimation by the image inpainting method may be further improved by first colorizing the IR image. In one or more embodiments, colorizing the IR image may use convolutional neural networks, as described in, e.g., i) "Learning representations for automatic colorization" by Gustav Larsson et al. published by Springer International Publishing in *European Conference on Computer Vision* in 2016, ii) "Colorful image colorization" by Richard Zhang et al. published by Springer International Publishing in *European Conference on Computer Vision* in 2016, and iii) "Let there be color!: joint end-to-end learning of global and local image priors for automatic image colorization with simultaneous classification" by Satoshi Iizuka et al. published on page 110 of *ACM Transactions on Graphics(TOG)* 35.4 in 2016. A background image may be generated using the image inpainting method with the colorized IR image and the mask image as input. The background image may then be converted back to gray scale for subsequent gas concentration-length calculation.

In one or more embodiments of the present invention, a gas concentration-length quantification system may include an OGI camera connected to a processor. The processor may perform one or more of the variations of the gas concentration-length method presented above to provide a gas concentration-length, a background radiance estimation, and/or a background temperature estimation.

In one or more embodiments, the processor may be integrated into a computing device. The computing device may be a mobile computer device (e.g., smart phone, tablet computer, laptop, e-reader, etc.), a desktop personal computer (PC), a kiosk, a server, a mainframe, a cable box, or the like. Each computing device may be operated by a user and may utilize one or more graphical user interfaces (GUIs) to generate requests from the user to calculate a gas concentration-length, a background radiance estimation, and/or a background temperature estimation and/or display information to the user. The user requests may specify an output location (e.g., display device, storage location, printer, etc.) for calculated data. In one or more embodiments, various components of a computing device may be combined to create a single component. Similarly, the functionality performed by a single component may be performed by two or more components.

In one or more embodiments, the computing device may include a plurality of computing devices that are connected.

In one or more embodiments, the OGI camera may also by integrated into the computing device.

One or more image frames acquired by an infrared (IR) optical gas imaging (OGI) cameras may be transferred to at least one of the user computing devices for processing and storing.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), performs one or more embodiments of the invention. Also, all discussed steps performed by a processor executing software instructions may, in one or more embodiments, be in the form of hardware such as circuitry. Those skilled in the art will appreciate that the hardware may be comprised of application-specific integrated circuits or other appropriate circuitry.

Further, one or more elements of the aforementioned computing device may be located at a remote location and connected to the other elements over a network. Further, one or more embodiments of the invention may be implemented on a distributed system having a plurality of nodes, where each portion of the invention may be located on a different node within the distributed system. In one or more embodiments of the invention, the node corresponds to a distinct computing device. Alternatively, the node may correspond to a processor with associated physical memory. The node may alternatively correspond to a processor or micro-core of a processor with shared memory and/or resources.

Although one or more embodiments of the present invention have been described with reference to the infrared portion of the spectrum, one skilled in the art will readily recognize that the method disclosed in the present invention may also be applied to radiation of other wavelengths.

While the invention has been described with respect to a limited number of embodiments, those skilled in the art, having benefit of this disclosure, will appreciate that other embodiments can be devised without departing from the scope of the invention as disclosed herein. Accordingly, the scope of the invention should be limited only by the attached claims.

What is claimed is:

1. A gas concentration-length quantification method, comprising:
    acquiring a first image including a gas plume with a camera;
    identifying and segmenting pixels corresponding to the gas plume in the first image;
    creating a mask image corresponding to the first image, wherein only pixels of the mask image corresponding to the gas plume in the first image have non-zero values;
    generating a background image corresponding to the first image using an image inpainting algorithm with the first image and the mask image as inputs;
    calculating a gas concentration-length for each pixel corresponding to the gas plume in the first image, based on the first image and the background image data; and
    triggering an alert when the gas concentration-length for at least one pixel exceeds a threshold level.

2. The method according to claim 1, wherein the camera is an optical gas imaging camera sensitive to infrared radiation and the first image is an infrared image.

3. The method according to claim 1, wherein the mask image is a binary image.

4. The method according to claim 1, further comprising selecting a region of interest enclosing the gas plume,
    wherein at least one step of the group of steps consisting of creating a mask image, generating a background image, and calculating the gas concentration-length is performed within the region of interest.

5. The method according to claim 4, wherein the region of interest encloses a substantially homogeneous background scene.

6. The method according to claim 1, further comprising:
    colorizing the first image;
    converting the generated background image back to a gray scale image prior to calculating the gas concentration-length for each pixel,
    wherein the generated background image uses the colorized first image as an input and is colorized.

7. The method according to claim 6, wherein colorizing the first image uses a convolutional neural network.

8. The method according to claim 1, wherein the image inpainting method is a Telea algorithm.

9. The method according to claim 1, wherein the image inpainting method is a Navier-Stokes algorithm.

10. A gas concentration-length quantification system, comprising:
    a camera;
    a processing unit connected to the camera,
    wherein the processor performs:
        reading a first image including a gas plume from the camera;
        identifying and segmenting pixels corresponding to the gas plume in the first image;
        creating a mask image corresponding to the first image wherein only pixels of the mask image corresponding to the gas plume in the first image have non-zero values;
        generating a background image corresponding to the first image using an image inpainting algorithm with the first image and the mask image as inputs;
        calculating a gas concentration-length for each pixel corresponding to the gas plume in the first image, based on the first image and the background image data; and
        triggering an alert when the gas concentration-length for at least one pixel exceeds a threshold level.

11. The system according to claim 10, wherein the camera is an optical gas imaging camera sensitive to infrared radiation and the first image is an infrared image.

12. The system according to claim 10, wherein the mask image is a binary image.

13. The system according to claim 10, further comprising selecting a region of interest enclosing the gas plume,
    wherein at least one step of the group of steps consisting of creating a mask image, generating a background image, and calculating the gas concentration-length is performed within the region of interest.

14. The system according to claim 13, wherein the region of interest encloses a substantially homogeneous background scene.

15. The system according to claim 10, further comprising:
    colorizing the first image;
    converting the generated background image back to a gray scale image prior to calculating the gas concentration-length for each pixel,
    wherein the generated background image uses the colorized first image as an input and is colorized.

16. The system according to claim 15, wherein colorizing the first image uses a convolutional neural network.

17. The system according to claim 10, wherein the image inpainting method is a Telea algorithm.

18. The system according to claim 10, wherein the image inpainting method is a Navier-Stokes algorithm.

19. A non-transitory computer readable medium (CRM) storing computer readable program code embodied therein that:
    reads a first image including a gas plume;

identifies and segments pixels corresponding to the gas plume in the first image;

creates a mask image corresponding to the first image wherein only pixels of the mask image corresponding to the gas plume in the first image have non-zero values;

generates a background image corresponding to the first image using an image inpainting algorithm with the first image and the mask image as inputs;

calculates a gas concentration-length for each pixel corresponding to the gas plume in the first image, based on the first image and the background image data; and triggers an alert when the gas concentration-length for at least one pixel exceeds a threshold level.

\* \* \* \* \*